US009987086B2

(12) United States Patent
Edmunds et al.

(10) Patent No.: US 9,987,086 B2
(45) Date of Patent: Jun. 5, 2018

(54) MULTIPLE ELECTRODE RF ABLATION CATHETER AND METHOD (71) Applicant: Boston Scientific Scimed, Inc., Maple Grove, MN (US)

(72) Inventors: Kevin D. Edmunds, Ham Lake, MN (US); Mark L. Jenson, Greenfield, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 865 days.

(21) Appl. No.: 13/973,122

(22) Filed: Aug. 22, 2013

(65) Prior Publication Data
US 2014/0058374 A1  Feb. 27, 2014

Related U.S. Application Data (60) Provisional application No. 61/692,047, filed on Aug. 22, 2012.

(51) Int. Cl.
*A61B 18/14* (2006.01)
*A61B 18/18* (2006.01)
*A61B 18/00* (2006.01)

(52) U.S. Cl.
CPC .......... *A61B 18/18* (2013.01); *A61B 18/1492* (2013.01); *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/00875* (2013.01); *A61B 2018/1467* (2013.01)

(58) Field of Classification Search
CPC ....... A61B 18/04; A61B 18/08; A61B 18/082; A61B 18/10; A61B 18/12; A61B 18/1266; A61B 18/14; A61B 18/1442; A61B 18/1445; A61B 18/1448; A61B 18/1492; A61B 18/18; A61B 2018/00404; A61B 2018/00434; A61B 2018/00511; A61B 2018/00577; A61B 2018/00791; A61B 2018/00875; A61B 2018/1467
USPC ...................................... 606/33–50
See application file for complete search history.

(56) References Cited

U.S. PATENT DOCUMENTS

| | | | |
|---|---|---|---|
| 6,350,263 B1 * | 2/2002 | Wetzig | A61B 18/1492 600/374 |
| 2002/0026127 A1 * | 2/2002 | Balbierz | A61B 18/1206 600/567 |
| 2006/0079886 A1 * | 4/2006 | Orszulak | A61B 18/1206 606/41 |
| 2007/0055322 A1 * | 3/2007 | Forsberg | A61N 1/36017 607/59 |

(Continued)

Primary Examiner — Michael Peffley
Assistant Examiner — Khadijeh Vahdat (57) ABSTRACT Disclosed herein, among other things, are methods and apparatus related to radio frequency (RF) ablation catheters. The present subject matter provides an ablation catheter system including an ablation catheter, multiple RF electrodes positioned along a distal end of a catheter, an electrical stimulation generator, and a control circuit electrically connected to the stimulation generator. According to various embodiments, the RF electrodes are each connected to the stimulation generator using a switch, and the control circuit is configured to distribute RF power from the stimulation generator to the RF electrodes using the switches to provide ablation therapy.

8 Claims, 5 Drawing Sheets (56) References Cited

U.S. PATENT DOCUMENTS

2009/0137952 A1* 5/2009 Ramamurthy ........... A61B 5/06
604/95.01

* cited by examiner

MULTIPLE ELECTRODE RF ABLATION CATHETER AND METHOD

CLAIM OF PRIORITY

This application claims the benefit of priority under 35 U.S.C. § 119(e) of U.S. Provisional Patent Application Ser. No. 61/692,047, filed on Aug. 22, 2012, which is herein incorporated by reference in its entirety.

TECHNICAL FIELD

This application relates generally to medical devices and, more particularly, to systems and methods related to ablation catheters.

BACKGROUND

Renal sympathetic nerves have been identified as a contributor to hypertension, as patients with hypertension exhibit increased sympathetic activity relating to the kidneys. Ablation of renal nerves is one way of treating hypertension. In radio frequency (RF) ablation, RF energy is directed from the ablation electrode through tissue to ablate the tissue and form a lesion.

RF electrodes in the renal artery can ablate renal nerves to treat hypertension, but can also damage the artery. To avoid circumferential artery damage, an RF electrode is repositioned at multiple spaced ablation targets, increasing treatment time and inconvenience, as accurate positioning can prove difficult. Using multiple electrodes can reduce time and repositioning problems, but the electrodes may need to be independently controlled. Prior independent electrode catheters are bulky and stiff, and control units with multiple generators are complicated and expensive.

What is needed in the art is an improved RF ablation catheter system with multiple electrodes.

SUMMARY

Disclosed herein, among other things, are methods and apparatus related to radio frequency (RF) ablation catheters. The present subject matter provides an ablation catheter system including an ablation catheter, multiple RF electrodes positioned along a distal end of a catheter, an electrical stimulation generator, and a control circuit electrically connected to the stimulation generator. The RF electrodes are each connected to the stimulation generator using a switch, and the control circuit is configured to distribute RF power from the stimulation generator to the RF electrodes using the switches to provide ablation therapy.

Another aspect of the present subject matter includes a method of heating tissue using an ablation catheter having multiple RF electrodes. The method includes receiving RF power from an electrical stimulation generator, and distributing the RF power among multiple RF electrodes along an ablation catheter using switches. According to various embodiments, the RF power is used to heat tissue, for example to provide RF ablation therapy.

One aspect of the present subject matter provides an ablation catheter system including an ablation catheter having a radio frequency (RF) power wire and multiple RF electrodes positioned along a distal end of a catheter. An electrical stimulation generator is connected to the RF power wire, and a control circuit is electrically connected to the stimulation generator. According to various embodiments, the RF electrodes are each connected to the control circuit using an optical fiber, a control LED, and an optical switch connected to the RF power wire. The control circuit is configured to provide control of power to the multiple RF electrodes using the stimulation generator to provide ablation therapy, according to various embodiments.

A further aspect of the present subject matter includes a method for ablating tissue using an ablation catheter having multiple RF electrodes. The method includes receiving RF power from a single electrical stimulation generator, and distributing the RF power among multiple RF electrodes along an ablation catheter using electrical control wires and solid state switches. According to various embodiments, RF ablation therapy is provided to a renal nerve to treat hypertension.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an," "one," or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein, among other things, are methods and apparatus related to radio frequency (RF) ablation catheters. The present subject matter provides an ablation catheter system including an ablation catheter, multiple RF electrodes positioned along a distal end of a catheter, an electrical stimulation generator, and a control circuit electrically connected to the stimulation generator. The RF electrodes are each connected to the stimulation generator using a switch, and the control circuit is configured to distribute RF power from the stimulation generator to the RF electrodes using the switches to provide ablation therapy.

The present subject matter provides systems and methods for ablating renal nerves for the treatment of hypertension, in various embodiments. Other types of tissue heating and ablation can be performed using the present systems and methods, with departing from the scope of the present subject matter. Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves via renal denervation can reduce blood pressure, and may be a viable treatment option for many patients with hypertension who do not respond to conventional drugs.

Figure 1:
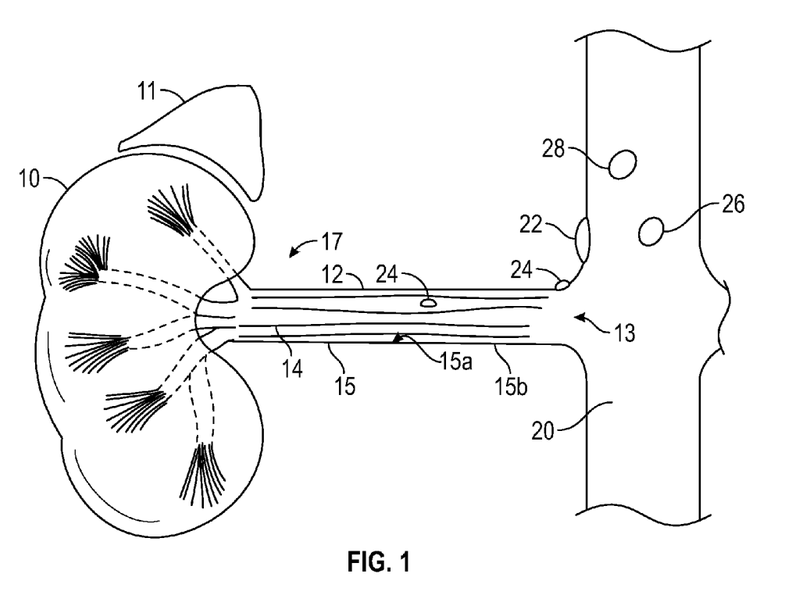
FIG. 1 is an illustration of a kidney and selected renal nerves and vasculature.

FIG. 1 is an illustration of a kidney 10 and renal vasculature including a renal artery 12 branching laterally from the abdominal aorta 20. The right and left kidneys are supplied with blood from the right and left renal arteries that branch from respective right and left lateral surfaces of the abdominal aorta 20. The right and left renal arteries extend from the abdominal aorta 20 to respective renal sinuses proximate the hilum 17 of the kidneys, and branch into segmental arteries and then interlobular arteries within the kidney 10. Also shown in FIG. 1 is the suprarenal gland 11, commonly referred to as the adrenal gland.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

Figure 2A:
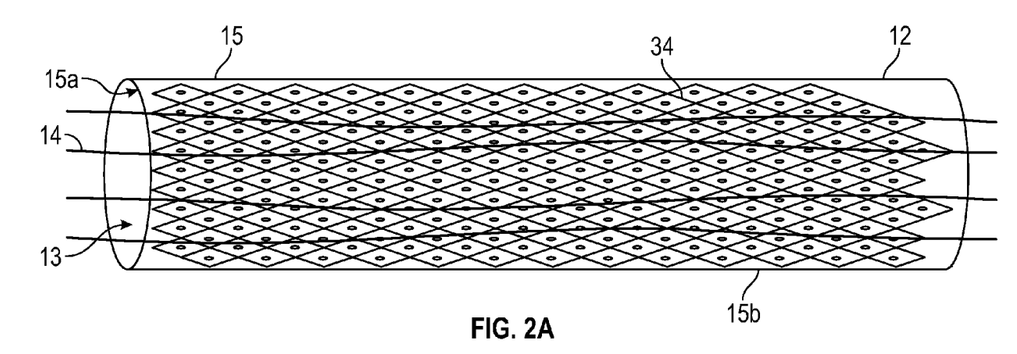
FIGS. 2A-2B illustrate innervation associate with the renal artery.
Figure 2B:
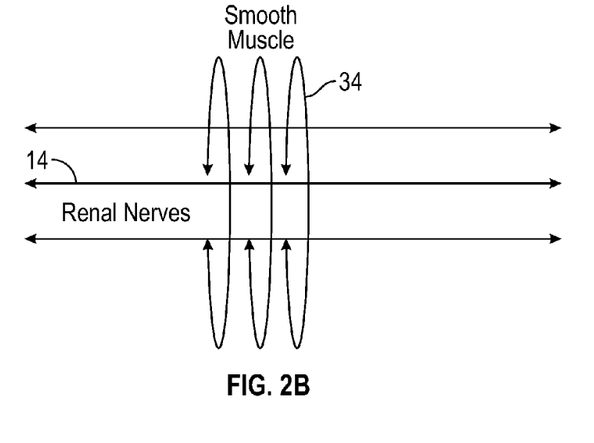

The kidneys and ureters are innervated by the renal nerves 14. FIGS. 1 and 2A-2B illustrate sympathetic innervation associated with the renal vasculature, primarily innervation of the renal artery 12. The primary functions of sympathetic nerves associated with the renal vasculature include signaling to and from the kidney, regulation of renal blood flow and pressure, stimulation of renin release, and direct stimulation of water and sodium ion reabsorption.

Most of the nerves innervating the renal vasculature are sympathetic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

The renal artery 12 is lined with smooth muscle 34 that controls the diameter of the renal artery lumen 13. The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14. The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3A:
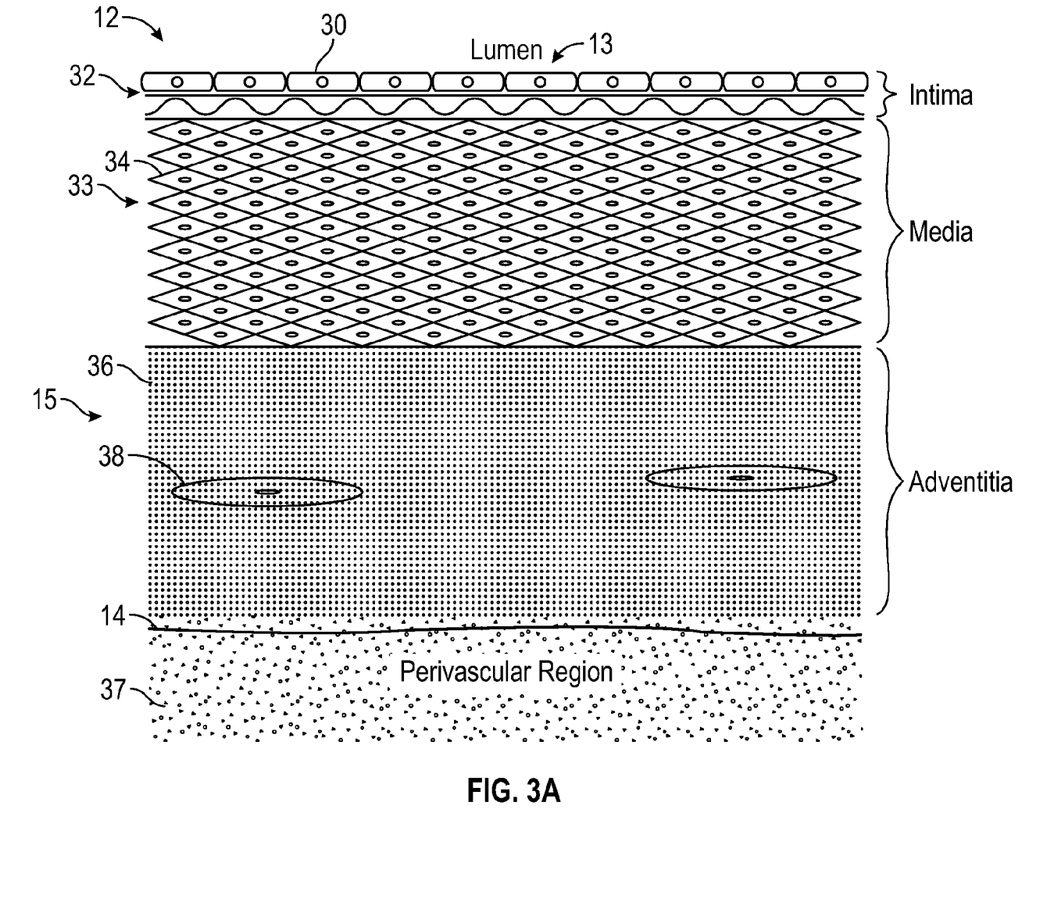
FIGS. 3A-3C illustrate various portions of the renal nerve and artery.

FIG. 3A shows a segment of a longitudinal cross-section through a renal artery, and illustrates various tissue layers of the wall 15 of the renal artery 12. The innermost layer of the renal artery 12 is the intima, which is lined with endothelium 30, which is supported by an internal elastic lamina 32. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, including the inner elastic lamina 32.

Adjacent the intima is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is largely made up of connective tissue. The adventitia 36 includes fibroblast cells 38 that play an important role in wound healing.

Figures 3B, 3C:
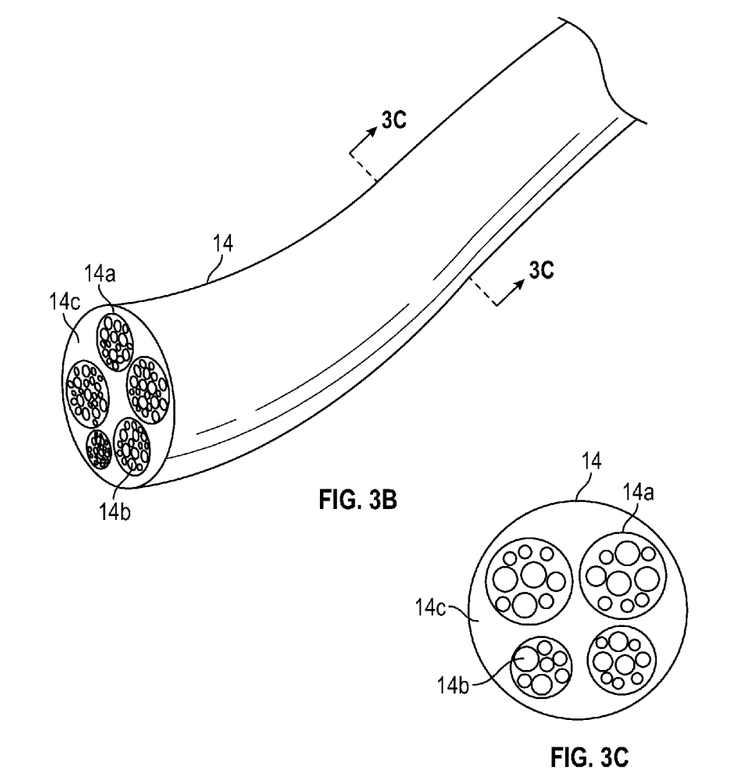

A perivascular region 37 is shown adjacent and peripheral to the adventitia 36 of the renal artery wall 15. A renal nerve 14 is shown proximate the adventitia 36 and passing through a portion of the perivascular region 37. The renal nerve 14 is shown extending substantially longitudinally along the outer wall 15 of the renal artery 12. The main trunk of the renal nerves 14 generally lies in or on the adventitia 36 of the renal artery 12, often passing through the perivascular region 37, with certain branches coursing into the media 33 to innervate the renal artery smooth muscle 34. Bundles 14a of nerve fibers 14b each comprise axons or dendrites that originate or terminate on cell bodies or neurons located in ganglia or on the spinal cord, or in the brain. Supporting tissue structures 14c of the nerve 14 include the endoneurium (surrounding nerve axon fibers), perineurium (surrounds fiber groups to form a fascicle), and epineurium (binds fascicles into nerves), which serve to separate and support nerve fibers 14b and bundles 14a.

In some embodiments, a treatment apparatus of the disclosure may be implemented to deliver denervation therapy that causes transient and reversible injury to renal nerve fibers 14b. In other embodiments, a treatment apparatus of the disclosure may be implemented to deliver denervation therapy that causes more severe injury to renal nerve fibers 14b, which may be reversible if the therapy is terminated in a timely manner. In still other embodiments, a treatment apparatus of the disclosure may be implemented to deliver denervation therapy that causes even more severe injury to renal fibers 14b, which may be irreversible.

Figure 4:
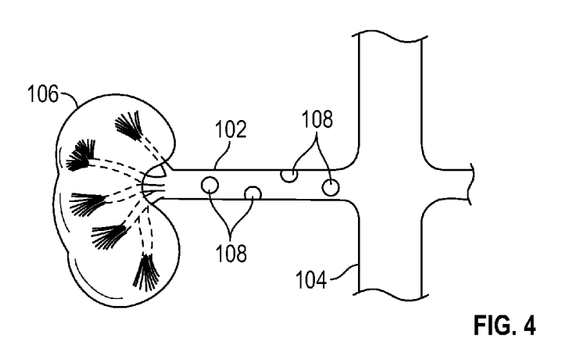
FIG. 4 illustrates ablation sites along the renal artery.

FIG. 4 illustrates ablation sites 108 along the renal artery 102, which connects a kidney 106 to the aorta 104. Ablation of perivascular renal nerves has been used as a treatment for hypertension. RF electrodes on catheters placed in the renal artery can be used to ablate the nerves, but with risk of artery wall injury. To control injury to the artery wall, one method is to move the RF electrode to ablate at discrete locations along and around the artery; this can cause local renal artery injury due to the local high temperatures resulting from high current density near the electrodes, but reduces the potential for significant stenotic narrowing of the artery after the ablation procedure. In some approaches, a spiral pattern of ablation spots has been used to ablate the nerves while minimizing injury to the vessel wall. However, reliably positioning the electrode to ensure the desired relative spacing between ablation spots has been difficult, and repeated ablation cycles is also time-consuming. Various multiple-electrode devices have been conceived to overcome the problem of repositioning. In some cases, it is desirable to independently sense impedance at each electrode, and/or to independently power each electrode, to distribute the ablation energy as desired. Separate control unit functions for each electrode can be costly to incorporate. Separate electrical wires for sensing and power for each electrode can be bulky and stiff. An improved system for independently sensing and powering each RF electrode is needed.

Figure 5:
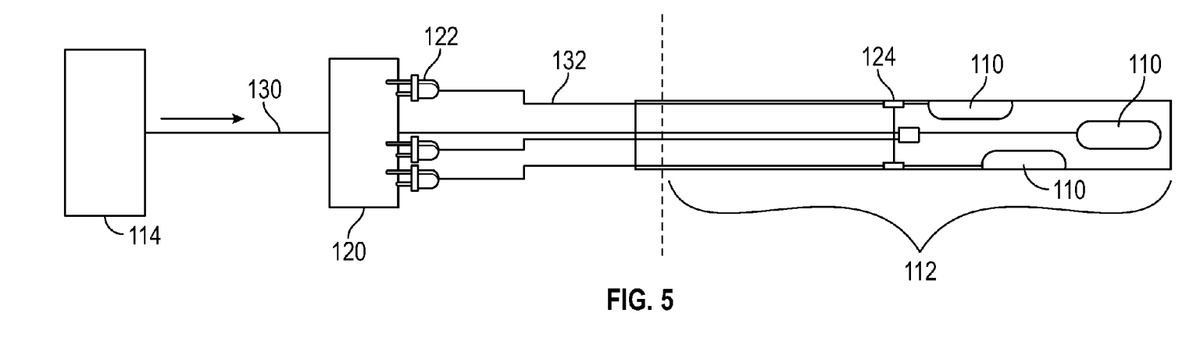
FIG. 5 illustrates an ablation catheter system with multiple electrodes, according to various embodiments of the present subject matter.

FIG. 5 illustrates an ablation catheter system with multiple electrodes, according to various embodiments of the present subject matter. An ablation catheter 112 and system is provided with multiple RF independent electrodes 110 for more effective target ablation with less damage to non-target tissue. Power switching takes RF power from a generator 114 and distributes it among multiple electrodes using control LEDs or electrical control wires 122 as part of a control circuit 120 and solid state or optical switches 124 near the tip. A wire 130 provides RF power to each electrode as needed, with fine optical fibers 132 along the catheter for control signals, reducing catheter size and stiffness. Sensor information (temperature, impedance) can be used to control the power switches in a closed loop feedback system. Embodiments of the present subject matter may use a single RF generator to provide control of multiple independent electrodes.

RF power can be cycled to each electrode in rapid succession or to all electrodes simultaneously, or in other combinations as needed. In one embodiment, sensing monitors impedance, and impedance levels or changes can be used to determine which electrodes should be energized, and for how long, to deliver the desired ablation energy. If additional sensor information is needed (temperature, etc.), optical fibers or fine wires can be incorporated for them. For example, if one spot has a temperature that is too high or rising too fast, the corresponding electrode can be given less power or turned off completely. If some spots have impedance changes that indicate more or less heating, or improper artery wall contact, power to the corresponding electrodes can be adjusted appropriately. In some cases, sensor information can be converted to optical data and transmitted via fine optical fibers as well. To deliver more or less overall power, the output of the generator can be adjusted. To deliver more or less power to a particular electrode, the solid state optical switches can be switched on and off over time, varying the duty cycle as needed. This subject matter can be used with wall-contact and off-wall electrodes, and can be used with bipolar configurations, or with unipolar configurations using a ground pad, in various embodiments.

Figure 6:
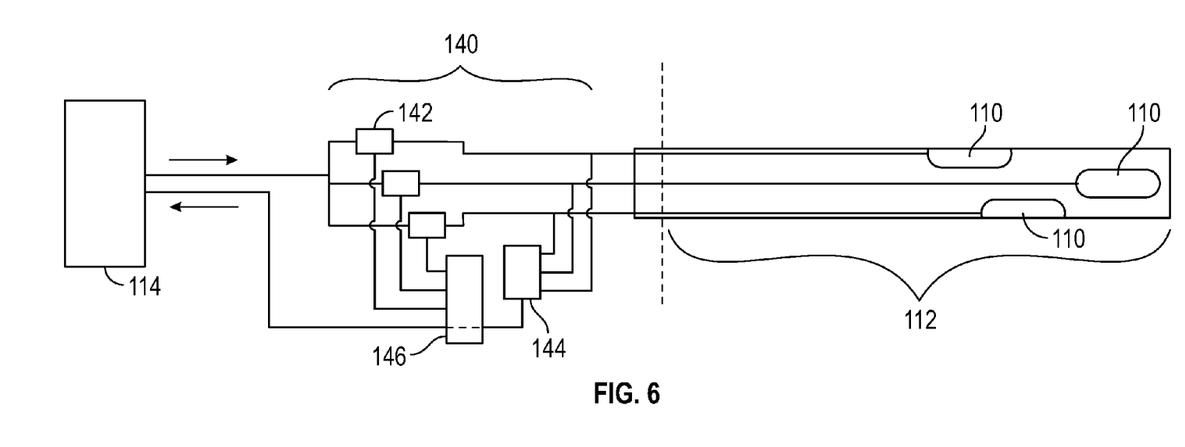
FIG. 6 illustrates an ablation catheter system with multiple electrodes using solid state switching, according to various embodiments of the present subject matter.

FIG. 6 illustrates an ablation catheter system with multiple electrodes using solid state switching, according to various embodiments of the present subject matter. An RF ablation catheter 112 and system incorporating multiple ablation electrodes 110 that can be independently controlled to provide more effective target ablation (renal nerves, etc.) with less damage to non-target tissue. A power switching feature may be used to take RF power from a generator 114 and distribute it among multiple electrodes 110 using field-effect transistor (FET) switches 142 or other similar solid-state elements. RF power can be provided to each electrode as needed. Information from sensors 144 (temperature, impedance) can be used to further control the power switches 142. The control unit 140 or control circuit includes a microcontroller 146 connected to the sensors 144 and to the switches 142, in various embodiments. The present subject matter may use a single generator 114 to provide control of multiple independent electrodes 110. The switching components 142 can be incorporated into the control unit, or into the catheter hub, or into an intermediate connector, in various embodiments.

RF power can be cycled to each electrode in rapid succession or to all electrodes simultaneously, or in other combinations as needed. Sensor information (temperature, impedance) can also be switched for a single input to the control unit, or multiple sensors can be used to modulate the timing or power to each electrode by controlling the power switches. For example, if one spot has a temperature that is too high or rising too fast, the corresponding electrode can be given less power or turned off completely. If some spots have impedance changes that indicate more or less heating, or improper artery wall contact, power to the corresponding electrodes can be adjusted appropriately. This subject matter can be used with wall-contact and off-wall electrodes, and can be used with bipolar configurations, or with unipolar configurations using a ground pad, in various embodiments.

One of ordinary skill in the art will understand that, the modules and other circuitry shown and described herein can be implemented using software, hardware, and/or firmware. Various disclosed methods may be implemented as a set of instructions contained on a computer-accessible medium capable of directing a processor to perform the respective method.

This application is intended to cover adaptations or variations of the present subject matter. It is to be understood that the above description is intended to be illustrative, and not restrictive. For example, the present subject matter can be applied to other medical procedures where heating or ablation of tissue is desired. The scope of the present subject matter should be determined with reference to the appended claims, along with the full scope of legal equivalents to which such claims are entitled.

What is claimed is:

1. An ablation catheter system, comprising:
    an ablation catheter;
    multiple RF electrodes positioned along a distal end of the ablation catheter;
    multiple optical switches incorporated into the ablation catheter;
    at least one sensor for the multiple RF electrodes, wherein sensor information from the at least one sensor is converted to optical data and transmitted via an optical fiber;
    an electrical stimulation generator; and
    a control circuit electrically connected to the electrical stimulation generator;
    wherein the multiple RF electrodes are each connected to the electrical stimulation generator using a separate one of said multiple optical switches, and the control circuit is configured to distribute RF power from the electrical stimulation generator to the multiple RF electrodes using the multiple optical switches to provide ablation therapy.

2. The ablation catheter system of claim 1, wherein the multiple optical switches are incorporated into the control circuit.

3. The ablation catheter system of claim 1, wherein the multiple optical switches are positioned near a distal end of the ablation catheter.

4. The ablation catheter system of claim 1, wherein the system is configured to deliver ablation therapy to a renal nerve to treat hypertension.

5. An ablation catheter system, comprising:
    an ablation catheter including a radio frequency (RF) power wire;
    multiple RF electrodes positioned along a distal end of the ablation catheter;
    multiple optical switches incorporated into the ablation catheter;
    at least one sensor configured to sense a sensed parameter for the multiple RF electrodes, wherein sensor information from the at least one sensor is converted to optical data and transmitted via an optical fiber;
    an electrical stimulation generator connected to the RF power wire; and
    a control circuit electrically connected to the electrical stimulation generator;
    wherein the multiple RF electrodes are each connected to the control circuit using a separate optical fiber, a separate control LED, and a separate one of said multiple optical switches connected to the RF power wire, and the control circuit is configured to distribute RF power from the electrical stimulation generator to the multiple RF electrodes using the multiple optical switches to provide ablation therapy to a renal nerve to treat hypertension.

6. The ablation catheter system of claim 5, wherein the multiple optical switches are positioned near a distal end of the ablation catheter.

7. The ablation catheter system of claim 5, wherein the multiple optical switches can be switched on and off with a variable duty cycle, and wherein the duty cycle is controlled to control the ablation therapy.

8. The ablation catheter system of claim 5, wherein the control circuit is configured to use the sensed parameter to adjust the ablation therapy.

* * * * *